United States Patent [19]
Carter

[11] Patent Number: 5,132,292
[45] Date of Patent: Jul. 21, 1992

[54] TREATMENT OF VIRAL HEPATITIS

[75] Inventor: William A. Carter, Birchrunville, Pa.

[73] Assignee: Hem Research, Inc., Rockville, Md.

[21] Appl. No.: 528,962

[22] Filed: May 25, 1990

[51] Int. Cl.$^5$ .............................................. A51K 31/70
[52] U.S. Cl. .................................... 514/44; 514/46
[58] Field of Search .................................. 514/44, 46

[56] References Cited

U.S. PATENT DOCUMENTS 4,950,652  8/1990  Carter .................................. 514/44
4,963,532 10/1990  Carter .................................. 514/44

OTHER PUBLICATIONS

Morbidity and Mortality Report 31(24): 317.
Beasley, R. P. et al:Hepatocellular carcinoma and Lanacet 2:1129, 1981.
Shafritz et al Integration of hepatitis B . . . specimens New England Journal of Medicine 305:1067, 1981.
Zaman et al Ris factors in Development . . . cirrhosis Lancet 1:1357, 1985.
kuhns et al New Assay for quantitative . . . human serum Zuckerman 45th ed. Alan R. Liss N.Y. 1988.
Scullard et al Antiviral treatment of chronic . . . infection Hepatology 1:228–232, 1981.
Scullard et al Antiviral treatment of chronic . . . to treatment Hepatology 2:39–49, 1982.

*Primary Examiner*—John W. Rollins
*Attorney, Agent, or Firm*—Nixon & Vanderhye

[57] ABSTRACT

Hepatitis viral infections are efficaciously treated with mismatched dsRNAs, notably $rI \cdot r(C_{11-14},U)_n$, alone or in combination with one or more of ganciclovir, coumermycin Al, dideoxyinosine or its nucleoside analogs.

9 Claims, No Drawings

TREATMENT OF VIRAL HEPATITIS

Viral hepatitis is characterized by a newly uncovered deficiency in intracellular dsRNA of a specific molecular configuration. This dsRNA is necessary to "drive" certain host defense pathways. The biochemical deficiencies are manifested in liver hepatocytes as well as in certain peripheral blood cells of the lymphoid series. The deficiency is associated with simultaneous multiplication of disparate viruses—hepatitis, retroviruses and herpes—often with the same individual. Exogenously supplied dsRNA of specific configurations addresses the deficiency with a resultant salutatory clinical improvement. The invention disclosed relates to therapeutic regimes for various types of viruses associated with liver damage such as hepatitis A, B and non A-B virus.

BACKGROUND OF THE INVENTION

Chronic hepatitis B viral infection (HBV) is an enormous global health concern. Approximately 200 million individuals world wide may be chronically infected with HBV. These infected individuals represent a catastrophic health risk individually, but further represent a major threat of infectivity and magnification of this global epidemic. In the United States 0.1 to 0.5% of all normal, healthy blood donors are hepatitis B surface antigen (HBsAG) positive [1]. In a selected population of individuals at high risk for infection (health care professionals, hemophiliacs, hemodialysis patients, and needle-using drug addicts), the percentage of HBsAg positivity may be as high as 30 percent. Chronic HBV carriers may transmit infection by blood contact or sexual contact. Some HBV carriers are of special concern, especially dentists, physicians, or other health care professionals, which have been documented to spread infection to multiple patient contacts.

Hepatitis B viral infection, typically self limited, can result in a chronic infective state. Ten percent of all HBV infections may result in a chronic viral infection, including: (1) chronic persistent infection and, (2) chronic active infection. The former (chronic persistent infection) often renders the patient asymptomatic or mildly symptomatic but still infectious. The latter (chronic active infection) carries a significant risk of severe debilitation as well as life-threatening manifestations such as cirrhosis, portal hypertension, and death. Hepatocellular carcinoma is also strongly correlated with chronic HBV infection[2-4]. Symptoms experienced by patients with chronic HBV infection vary from none to mild degrees of fatigue, malaise, myalgia, arthralgia, and pruritis to more severe manifestations of liver dysfunction (such as bleeding disorders, ascites, and encephalopathy). Biochemical abnormalities associated with chronic HBV include an elevation of liver transaminases in the serum, a reduction in serum albumin, elevation of serum bilirubin and prolongation of the prothrombin time (in advanced end-stage liver disease). Hepatitis viruses may be transmitted by human fluids, feces, sexual contact, etc.

Persistent elevation of HBsAg historically has been used as a marker for chronic HBV infection, in conjunction with other pertinent serologic markers. Traditional serologic tests are qualitative; HBsAg titers do not correlate with severity of infection and do not necessarily imply infectivity. In recent years, a hybridization assay with radiolabeled cDNA against HBsAg-DNA (HBV-DNA) has been devised. Direct assay of HBV-DNA allows increased specificity (false positive HBsAg can occur infrequently) and vastly increased sensitivity in detecting HBV infection. Traditional HBV-DNA assay is semiquantitative; slot-blot hybridization with radiolabeled probe cDNA against a serum sample from an infected host can yield an autoradiogram that can be scanned by densitometry to yield an estimate of sample signal intensity which is then correlated to an approximate quantity of HBV-DNA.

Alternatively, a solution hybridization assay using an $I^{125}$ labelled cDNA probe of digested samples have been devised by Abbott Labs., Chicago, IL.[5]. This assay utilizes fluid phase hybridization, single step column chromatography and direct quantitation of HBV-DNA by gamma-emission. The limit of detection is said to be 1.5 picogram HBV-DNA/ml sera.

Effective therapy for HBV infection is important for at least three reasons:

1. Improvement in liver disease in patients with chronic active hepatitis: It has been shown that loss of hepatitis B viral particles (HBeAg and HBV-DNA) accompanying treatment with antivirals has been associated with improvement in histologic liver disease and decrease in levels of serum markers of liver inflammation[6].

2. Loss of infectivity in patients with chronic persistent and chronic active hepatitis: It has been shown that loss of DNA polymerase and HBeAg from sera is accompanied by loss of infectivity of patient sera for susceptible chimpanzees[7].

3. Decreased probability of hepatocellular carcinoma: Strongly supported for the first time by experiments I have performed herein.

Prior to this invention, there was no known treatment for chronic HBV infection and its associated disease. Recent reports have suggested interferon to be of transient benefit in treatment of some patients. Still, upwards of 75% of patients with chronic HBV infection fail to respond to interferon and sustained responses after cessation of interferon treatment are yet less frequent. Other forms of therapy are less efficacious and associated with frequent, undesirable toxic effects (i.e., adenosine arabinoside).

DESCRIPTION OF THE INVENTION

Viral hepatitis alone or associated with other viruses such as retroviruses and herpes viruses, is assessed by deficiencies in intracellular dsRNA of a specific molecular configuration in biological samples such as liver hepatocytes and certain peripheral blood cells of the lymphoid series. Viral hepatitis infections are treated with exogenously administered dsRNA or dsRNA in combination with one or more antiviral agents.

Disclosed are methods of diagnosing hepatitis virus infections, notably hepatitis B virus, in a patient by first assessing the level of intracellular 2'-5'A oligoadenylate synthetase in healthy individuals, aberrant 2'-5'A synthetase levels as compared with those in healthy individuals indicating the presence of a hepatitis virus infection, and thereafter, if necessary, administering an amount of a dsRNA sufficient to adjust the 2'-5'-oligoadenylate concentration to those of healthy individuals.

Also described are methods of treating hepatitis B virus infections in a patient including administering an effective amount of the combination of a mismatched dsRNA together with at least one of ganciclovir, foscarnet, coumeracycin A1 or a nucleoside analog. A retrovirus, a herpes virus or both may also be present in the patient.

Desirably, the mismatched dsRNA is a complex of a polyinosinate and polycytidylate containing from 1 in 5 to 1 in 30 uracil guanaidine bases, specifically the dsRNA is $rI_n \cdot r(C_{11-14},U)_n$ or a mismatched dsRNA containing regions of bond breakage and exhibiting the favorable therapeutic ratio property of $rI \cdot r(C_{11-14},U)_n$.

The amount of mismatched dsRNA administered results in a level of from 2 to 1,000 micrograms of the mismatched dsRNA per milliliter of the patient's systemic blood circulation. The other antiviral agent or agents, when used, are administered within their usual amounts according to the suppliers instructions.

Biologic Activity of Ampligen ®

Ampligen ® (poly I-poly $C_{12}U$, HEM Research, Inc., Rockville, MD) belongs to a class of molecules collectively referred to as double stranded (ds) RNA and is referred to herein as a prototypic dsRNA among several, as explained and illustrated in more detail below. Double stranded RNAs act as lymphokines, that is, molecules that mediate cellular immune and antiviral activities. Ampligen ®activity includes natural killer cell modulation, macrophage modulation, B-lymphocyte modulation, tumor necrosis factor modulation, interferon modulation (including alpha, beta, and gamma types) and modulation of interferon-induced intracellular enzymes (2-5A synthetase and a protein kinase). Clinically, Ampligen ® can stabilize T4 cell counts and increase delayed-type hypersensitivity reactions in patients with AIDS-Related Complex. An antineoplastic effect has also been demonstrated both in vitro and in clinical study.

It was previously assumed that Ampligen ®-elicited effects as an antigrowth, antiviral and immunommodulatory agent results from its influence on the interferon cascade. That is, Ampligen ® stimulates both interferon production and acts as a necessary factor for the interferon-induced, intracellular environment that is requisite for expression of an antiviral and antigrowth state. However, I now report that biologic antiviral activity ascribed to Ampligen ® cannot be attributed to interferon induction. Indeed, antiviral activity can be noted in some systems immediately following Ampligen ® treatment.

A double stranded RNA (i.e., poly I:poly c) was utilized clinically as an antineoplastic agent during the late 1970's, but abandoned because of severe, intolerable toxicity. Ampligen ® is a specific form of mismatched dsRNA in which uridylic acid (U) is substituted for every 12th cytodylic acid in a strand of polycytodylic acid that is annealed to a strand of polycytodylic acid. This "mismatching" of nucleotide base pairs creates a specific outpouching in the overall molecular configuration of Ampligen ®. This outpouching of the molecule allows retention of biologic activity but renders Ampligen ® non-toxic. More specifically, the outpouching renders molecules which directly address as replacement therapy the intracellular deficiency in dsRNA brought about by hepatitis infection and which contributes directly to disease morbidity.

Several patients were infected with herpes-6, a relatively new class of herpes virus only recently described. The virus has been variously called HBLV (human B cell lymphocyte virus) of HHV-6 (human herpes virus-6). The main features of this virus are its icosahedral symmetry with about 162 capsomers and a lipid membrane. Infected cells develop into large refractive cells and some patients may have up to 20–30% or more of their circulating lymphocyte cells (a certain type of lymphocyte of bone marrow or thymus lineage) infected. Following specific dsRNA therapy for several months, the percentage of infected cells falls dramatically.

The dsRNA may be a complex of a polyinosinate and a polycytidylate containing a proportion of uracil bases or guanidine bases, e.g., from 1 in 5 to 1 in 30 such bases (poly $I \cdot poly(C_{4-29}x > U$ or $G))$.

The dsRNA used in this invention may be of the general formula $rI_n \cdot r(C_{11-14},U)_n$ or $rI_n \cdot r(C_{12},U)_n$. Other suitable examples of dsRNA are discussed below.

By "mismatched dsRNA" are meant those in which hydrogen bonding (base stacking) between the counterpart strands is relatively intact, i.e., is interrupted on average less than one base pair in every 29 consecutive base pair residues. The term "mismatched dsRNA" should be understood accordingly.

The mismatched dsRNAs preferred for use in the present invention are based on copolynucleotides selected from poly $(C_n,U)$ and poly $(C_n,G)$ in which n is an integer having a value of from 4 to 29 and are mismatched analogs of complexes of polyriboinosinic and polyribocytidilic acids, formed by modifying $rI_n \cdot rC_n$ to incorporate unpaired bases (uracil or guanidine) along the polyribocytidylate $(rC_n)$ strand. Alternatively, the dsRNA may be derived from poly(I)·poly(C) dsRNA by modifying the ribosyl backbone of polyriboinosinic acid $(rI_n)$, e.g., by including 2'-O-methyl ribosyl residues. The mismatched complexes may be complexed with an RNA-stabilizing polymer such as lysine cellulose. These mismatched analogs of $rI_n \cdot rC_n$, preferred ones of which are of the general formula $rI_n \cdot (C_{11-14},U)_n$ or $rI_n 1 \cdot r(C_{29},G)_n$, are described by Carter and Ts'o in U.S. Pat. Nos. 4,130,641 and 4,024,222 the disclosures of which are hereby incorporated by reference. The dsRNAs described therein generally are suitable for use according to the present invention.

Other examples of mismatched dsRNA for use in the invention include:

poly (I) ·poly $(C_4,U)$
poly (I) ·poly $(C_7,U)$
poly (I) ·poly $(C_{13},U)$
poly (I) ·poly $(C_{22},U)$
poly (I) ·poly $(C_{20},G)$
poly (I) ·poly $(C_{29},G)$ and
poly (I) ·poly $C_{p23}G > p$ Another class of dsRNAs suited to the practice of this invention are short dsRNAs of defined structure, for example oligonucleotides of the formula:

$$5'lock\text{-}(I)_n\text{-}lock\ 3'$$

$$3'lock\text{-}(C)_m\text{-}lock\ 5'$$

where m and n are each more than 5 and less than 100, I is inosine monophosphate, C is cytidine monophosphate, and where the locks in one strand are complementary to locks in the opposite strand, or an oligonucleotide of the structure:

$$5'lock\text{-}[(I)_xA]_j\text{-}lock\ 3'$$

$$3'lock\text{-}[(C)_yU]_k\text{-}lock\ 3'$$

where x and y are each more than 5 and less than 25, j and k each at least 1 and less than 10, I and C are as identified above, A is a nucleotide which is not I, and U is a nucleotide which base pairs with A.

Alternatively, the short oligonucleotide may have the structure:

where n, m, I and C are as defined above.

These oligonucleotides may have substitutions in one strand not complementary to nucleotides in the opposite strand. Preferably these oligonucleotides are stabilized by internal registers of complementary heteropolymer and desirably the lock or hinge or both contain regions of complementary heteropolymer. These oligonucleotides desirably have single-stranded tails. These oligonucleotides are described in more detail in U.S. application Ser. No. 07/181,385 filed Apr. 14, 1988 to Gillespie and Carter and in corresponding PCT/US89/02172, the disclosures of which are hereby incorporated by reference. The oligonucleotides may be administered by various routes, including orally, with appropriate carriers.

Duck hepatitis B virus shares the unique replicative pathway as the human hepatitis B virus (hepadnaviruses) and was considered an ideal model for evaluating antiviral agents against human HBV. Hepatitis B virus has unique replicative pathway and very unique genomic conformation; a single-strand genome which hybridizes into a ds/ss DNA molecule. It integrates into the human genome and hepatitis B positive individuals have a several hundred fold increase in liver cancer. Of the two animal systems available for chronic HBV studies, ducks and woodchucks, ducks were initially selected because they don't bite. Thus, ducks represent a rational in vivo system for drug testing.

The general protocol used in these animal studies was as follows: Congenitally infected ducks who have become carriers of the DHBV were treated with Ampligen ® alone, Ampligen ® + ganciclovir (antiviral), and Ampligen ® + ganciclovir + coumermycin A1 (DNA gyrase inhibitor), nalidixic acid (less toxic and oral administration) can also be used. Serum viral levels were quantitated by DNA hybridization and by DHBV DNA polymerase activity. The viral load in the liver was determined by DNA hybridization.

I used mismatched dsRNA to treat congenitally infected ducks who had become carriers of the DHBV. Pekin-Aylesbury crossbred ducklings, with stable and equivalent levels of serum DHBV DNA, were treated with Ampligen ® alone or in combination with ganciclovir or ganciclovir and coumermycin A1. Ampligen ® (7.5 mg/kg) was administered alone by intraperitoneal (i.p.) injection daily for 28 consecutive days. To determine whether other antivirals added to Ampligen ® would obtain an unexpected synergistic effect, Ganciclovir (10 mg/kg/day) and coumermycin A1 (10 mg/kg/day or foscarnet or nucleoside analogues, such as dideoxyinosine (DDI), etc. were also given by i.p. injection or orally (p.o.) in divided doses daily for the last 14 days of Ampligen ® treatment. All treated ducks tolerated the therapeutic regimes. There was no loss of weight or adverse hematological, liver function, or renal function deterioration noted, indicating the specificity of the dsRNA replacement therapy.

The data that follow show several significant facts. Ducklings treated with Ampligen ® showed a significant decline in serum DHBV DNA levels during the first two weeks of treatment, which continued for the following two treatment weeks. Four weeks after the cessation of treatment, the serum viral DNA levels may begin to slowly return. However, when Ampligen ® was combined with other agents such as ganciclovir, the inhibition of serum DHBV during treatment was complete during treatment. A similar pattern was seen in the other Ampligen ® combination, such as Ampligen ®/ganciclovir/coumermycin A1 treated ducklings. Viral DNA polymerase levels also showed inhibition in all combination treatment groups. Quantitative dot blot analysis of the liver samples showed 360 viral genome equivalents (vge) per hepatocyte in the untreated control ducklings. After treatment with Ampligen ® alone, there was an 83% decrease in DHBV to 60 vge per hepatocyte. At four weeks post-treatment, the DHBV returned to the pretreatment level of 360 vge per cell. In ducklings treated with Ampligen ® plus ganciclovir, <20 vge/per cell (>94% inhibition) was observed. Results in the Ampligen ®/ganciclovir/coumermycin A1 treated ducklings were virtually identical to the Ampligen ®ganciclovir treated group.

These results demonstrate that Ampligen ®, alone or in combination with other antiviral agents, can cause significant inhibition of DHBV DNA replication, seen either indirectly in the sera from infected ducklings, or directly in the liver.

Clinical Studies in Humans

Four HIV positive patients with immunodeficiency, who were treated with Ampligen ® (200 mg, twice per week, i.v.) in an open label study, were found to have concurrent hepatitis B virus infection, as measured by high levels of HBV DNA in the serum as well as concurrent herpes (HHV6) infection. Three of the four patients exhibited decreases in their serum HBV DNA levels during Ampligen ® therapy. For example, one patient showed a decrease from a 2+ titer to a ½+ titer within three months of the initiation of therapy. Similarly, a second patient showed a decrease in serum HBV levels from 3+, beginning with four and one-half months of Ampligen ® therapy, which continued to a 2+. These results are indicative of therapeutic responses against HBV even in the face of concurrent HIV disease with its well established multiple deficiencies in immune function.

By monitoring the specific deficiency of intracellular dsRNA brought about by the hepatitis pathogen and the resultant 2'-5'A pathway behavior, I was able to devise a specific structure of exogenous dsRNA which contemporaneously treated more than 2 (simultaneous) viral pathogens.

Laboratory Studies

In parallel laboratory studies, I showed that the requisite natural dsRNA necessary to trigger appropriate antiviral/immunologic defenses was missing both within hepatocytes and peripheral lymphocytes. This intracellular dsRNA deficiency was manifested by aberrations in the 2'-5'A oligo A pathway which should have been appropriately up-regulated by the chronic viral infection(s) but was not. Following administration of appropriately configured mismatched dsRNAs, I was able to demonstrate normalization of host defense pathway associated with a concurrent drop in plasma viremia (hepatitis, HIV and herpes) in the various human and animal systems I describe above.

The 2'-5'oligoadenylate synthetase/RNase L pathway in peripheral blood lymphocytes was also studied. Diagnosis is conveniently conducted from a sample of the patients blood to analyze the peripheral blood cells for enzymatically deficient 2'-5'oligoadenylate (2'-5'A) using the procedures described by Carter et al in *The Lancet*, Jun. 6, 1987, 1286-1292. The aberrance once noted is compared to the test results of otherwise healthy individuals matched for gender and age, and is corrected by the exogenous administration of dsRNA, preferably a mismatched dsRNA, to improve the patient's clinical condition. During and at the conclusion of therapy, the patient is followed to ascertain his/her improvement on a cellular level, which usually precedes the clinical improvement by several weeks, and to determine the amount of dsRNA, if any, needed to maintain a normal 2-5'A synthetase/RNase L pathway and maintain or further reduce the patient's hepatitis B virus level.

The in vivo concentration of 2'-5'A molecules in normal individuals and subjects with hepatitis B virus is assessed as follows: Ethanol-soluble fractions of patient samples (Ficoll-Hypaque-prified peripheral blood lymphocytes) were analyzed for their 2'-5'A content in 2'-5'A core-cellulose assays (affinity chromatography) with poly U-{$^{32}$P}-pCp. In this assay, the ability of 2'-5'A-activated RNase L to hydrolyze poly(U) is used to determine the concentration of functional 2'-5'A.

Reference values were established by testing 15 normal subjects with no recent history of viral infections as evidenced by lack of liver damage, fever, absence of constitutional symptoms, rashes, etc. Concentrations of their lymphocyte 2'-5'A levels were determined using calibration curves obtained with authentic 2'-5'A molecules.

In addition, 2'-5'A concentration and molecular size may be quantitated by high pressure liquid chromatography (HPLC). Also ribosomal RNA cleavage assays may be used to assess biological functionality (activity) of the 2'-5'A-synthesized by the patient in vivo or to determine the level of activated RNase L in patient samples. Peripheral mononuclear blood cells are the preferred cells for analysis.

REFERENCES

1. Morbidity and Mortality Report 31(24):317.
Beasley, R.P., Hwang, L.Y., Lin, C.C., et al: Hepatocellular carcinoma and hepatitis B virus: a prospective study of 22,707 men in Taiwan. Lancet 2:1129, 1981.
3. Shafritz, D.A., Shouval, D., Sherman, H.I. et al: Integration of hepatitis B virus DNA into the genome of liver cells in chronic liver disease and hepatocellular carcinoma: studies in percutaneous liver biopsies and post-mortem tissue specimens. New England Journal of Medicine 305:1067, 1981.
4. Zaman, S.N., Melia, W.M., Johnson, R.D., et al: Risk factors in development of hepatocellular carcinoma in cirrhosis: prospective study of 616 patients. Lancet 1:1357, 1985.
5. Kuhns, M.S., McNamara, A.L., Cabal, C.M., et al: A new assay for the quantitative detection of hepatitis B viral DNA in human serum. Viral Hepatitis and Liver Disease. Zuckerman 45th ed. Alan R. Liss, New York, 1988.
6. Scullard, G.H., Andres, L.L., Greenberg, H.B., et al: Antiviral treatment of chronic hepatitis B infection: improvement in liver disease with interferon and adenine arabinoside. Hepatology 1:228-232, 1981.
7. Scullard, G.H., Greenberg, H.B., Smith, J.L., et al: Antiviral treatment of chronic hepatitis B infection: infectious virus cannot be detected in patient serum after permanent responses to treatment. Hepatology 2:39-49, 1982.

What is claimed is

1. A method of treating hepatitis virus infections in a patient having the same, comprising administering to said patient an effective amount of the combination of a mismatched dsRNA together with at least one of ganciclovir coumeracycin A1, foscarnet or dideoxyinosine.

2. The method of claim 1, in which the patient is infected with hepatitis A, B or non A-B virus.

3. The method of claim 1, in which a retrovirus, a herpes virus or both are also present in the patient.

4. The method of claim 1, in which the mismatched dsRNA is a polyadenylic acid complexed with polyuridylic acid.

5. The method of claim 4, in which the mismatched dsRNA is a complex of a polyinosinate and polycytidylate containing from 1 in 5 to 1 in 30 uracil guanaidine bases.

6. The method of claim 5, in which the mismatched dsRNA is $rI_n \cdot r(C_{11-14},U)_n$ or a mismatched dsRNA containing regions of bond breakage and exhibiting the favorable therapeutic ratio property of $rI \cdot r(C_{11-14},U)_n$.

7. The method of claim 4, in which the amount of mismatched dsRNA administered results in a level of from 2 to 1,000 micrograms of the mismatched dsRNA per milliliter of the patient's systemic blood circulation.

8. The method of claim 1, in which the dsRNA is a short oligonucleotide of defined structure of the formula:

$$5'lock\text{-}(I)_n\text{-}lock\ 3'$$

$$3'lock\text{-}(C)_m\text{-}lock\ 5'$$

where m and n are each more than 5 and less than 100, I is inosine monophosphate, C is cytidine monophosphate, or $$5'lock\text{-}[(I)_xA]_j\text{-}lock\ 3'$$

$$3'lock\text{-}[(C)_yU]_k\text{-}lock\ 3'$$

where x and y are each more than 5 and less than 25, j and k each at least 1 and less than 10, I and C are as identified above, A is a nucleotide which is not I, and U is a nucleotide which base pairs with A, or $$5'(I)_n\text{-}hinge\text{-}(C)_m 3'$$

where n, m I and C are as defined above, provided that the locks in one strand are complementary to locks in the opposite strand.

9. The method according to claim 8, in which the oligonucleotide is stabilized by internal registers of complementary heteropolymer and the lock or hinge or both contain regions of complementary heteropolymer.